United States Patent [19]

Narisada et al.

[11] 4,143,038
[45] Mar. 6, 1979

[54] CEPHALOSPORIN ANALOGUES

[75] Inventors: Masayuki Narisada, Ibaraki; Hiroshi Onoue, Osaka; Teruji Tsuji, Ibaraki; Yasuhiro Nishitani, Izumi; Mitsuru Yoshioka, Toyonaka; Yoshio Hamashima, Kyoto; Wataru Nagata, Nishinomiya, all of Japan

[73] Assignee: Shionogi & Co., Ltd., Osaka, Japan

[21] Appl. No.: 846,503

[22] Filed: Oct. 26, 1977

Related U.S. Application Data

[62] Division of Ser. No. 741,485, Nov. 12, 1976, abandoned.

[30] Foreign Application Priority Data

Nov. 12, 1975 [GB] United Kingdom ............... 46759/75
Dec. 4, 1975 [GB] United Kingdom ............... 49891/75

[51] Int. Cl.$^2$ ............................................. C07D 205/00
[52] U.S. Cl. ................................... 260/239 A; 544/90
[58] Field of Search ............................ 544/30, 90, 92; 260/239 A, 239 AL

[56] References Cited

U.S. PATENT DOCUMENTS 3,974,154  8/1976  Nayler et al. ............... 260/239 A X
4,013,653  3/1977  Wolfe ................................. 544/92 X

FOREIGN PATENT DOCUMENTS 133593  12/1974  Japan .......................................... 544/90

OTHER PUBLICATIONS

Chemical Abstracts, vol. 81, Abst. No. 37560f (1974) (Abst. of Christensen et al., Ger. Offen. 2,355,209).

*Primary Examiner*—John D. Randolph
*Attorney, Agent, or Firm*—Wenderoth, Lind & Ponack

[57] ABSTRACT

Potent antibacterial cephalosporin analogues of the following formula in forms of free acids, pharmaceutically acceptable salts, or esters preparable from penicillins through azetidinone derivatives by way of a new process, and utilizable as active ingredients in bactericidal compositions for pharmaceutical and veterinary use:

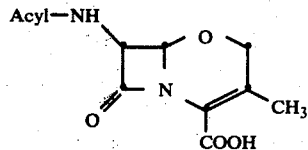

(wherein Acyl is selected from phenylacetyl, D-mandeloyl, α-phenylmalonyl, D-α-(3-methanesulfonyl-2-oxoimidazolidin-1-yl)carbonamido-α-phenylacetyl, and 2-thienylacetyl).

2 Claims, No Drawings

CEPHALOSPORIN ANALOGUES

This is a division of application Ser. No. 741,485, filed Nov. 12, 1976 (now abandoned).

This invention relates to certain cephalosporin analogues and to the preparation thereof.

According to the present invention there is provided a compound of the formula:

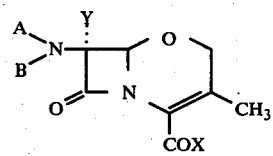

(wherein A and B are each hydrogen or an amino-protecting group;

X is hydroxy or a carboxy-protecting group; and

Y is hydrogen or methoxy;

provided that when A is hydrogen B cannot be hydrogen or phenylglycyl).

The compounds of the invention may be prepared effectively by the alignment of reactions set out below or by adapting suitable variations in the order of indivisual reactions.

So-called oxadethiacephalosporins and oxadethiapenicillins have been described by Christensen et al (Journal of the American Chemical Society, Volume 96, 7582 (1975)), and by Wolfe et al (Canadian Journal of Chemistry, Volume 52, 3996 (1974)) and in published patent applications filed by these scientists.

The amino-protecting group in the formula (I) can be acyl, silyl, sulfenyl, or hydrocarbyl group or other amino-protecting group containing up to 20 carbon atoms (including the corresponding groups in the side chains of natural or synthetic penicillins and cephalosporins).

The acyl groups for A and/or B in the formula (I) include inorganic acyls such as carbonic acyl (e.g. alkoxycarbonyl, aralkoxycarbonyl or aryloxycarbonyl), sulfuric acyl, phosphoric acyl (e.g. dialkoxyphosphinyl, dialkoxythiophosphonyl or alkoxyaminophosphoroyl); and organic acyls such as alkanoyl, cycloalkanoyl, aralkanoyl, aroyl, alkylsulfonyl, arylsulfonyl or alkylphosphonyl. These groups can, where possible, be interrupted by a hetero atom in their skeleton or can be unsaturated or they can be substituted by, for example, halogen (e.g. fluorine, chlorine or bromine), a nitrogen function (e.g. amino, hydrazino, azido, alkylamino, arylamino, acylamino, alkylideneamino, acylimino, imino or nitro), oxygen function (e.g. hydroxy, alkoxy, aralkoxy, aryloxy, acyloxy or oxo), sulfur function (e.g. mercapto, alkylthio, aralkylthio, arylthio, acylthio, thioxo, sulfo, sulfonyl, sulfinyl, alkoxysulfonyl or aryloxysulfinyl), carbon function (e.g. alkyl, alkenyl, aralkyl, aryl, carboxy, carbalkoxy, carbamoyl, alkanoyl, aroyl, aminoalkyl, aralkanoyl or cyano), or phosphorus function (e.g. phospho or phosphoroyl). A and B can also be considered together as forming a diacyl group of a polybasic acid (e.g. phthalyl, pyridine-2,3-dicarbonyl, maleoyl or succinoyl).

The hydrocarbon groups which may be represented by A and/or B can be easily removable aliphatic hydrocarbon groups containing from 1 to 20 carbon atoms (e.g. alkyl, alkenyl, aralkyl or other aliphatic hydrocarbon groups) or easily removable monocyclic aromatic hydrocarbon groups (e.g. phenyl or pyrimidyl). These groups can, where possible, be interrupted by a hetero atom in the skeleton thereof or can be unsaturated or they can be substituted by a substituent (e.g. halogen or by nitrogen, oxygen, sulfur, carbon, or phosphorus functions). A and B can also be considered together as forming a divalent hydrocarbon group (e.g. alkylene, aralkylene, alkylidene, aralkylidene, α-halo- or alkoxyaralkylidene, diarylmethylidene or cycloalkylidene), which can, where possible, be interrupted by a hetero atom in the skeleton thereof or can be substituted by a substituent cited above or can be unsaturated.

When group A is acyl and group B is a hydrocarbon group they can be combined together with the nitrogen atom bound to position 7 of the cephem ring to form a cyclic group (e.g. a 4-oxo-3-imidazolidinyl ring).

The silyl (e.g. trialkylsilyl) and sulfenyl (e.g. phenylsulfonyl or o-nitrophenylsulfenyl) groups which may be represented by A and/or B are conventional amino protecting groups.

Representative acyl groups for A in the above formula (I) include, when B is a hydrogen, the following groups:

(1) $C_1$ to $C_5$ alkanoyl;
(2) $C_2$ to $C_5$ haloalkanoyl;
(3) azidoacetyl;
(4) cyanoacetyl;
(5) acyl groups of the formula:

Ar—CQQ'—CO— in which Q and Q' are each hydrogen or methyl; and Ar is phenyl, dihydrophenyl or a monocyclic heterocyclic aromatic group containing from 1 to 4 hetero atoms, and may optionally be substituted by an inert group e.g. $C_1$ to $C_3$ alkyl or alkoxy, chlorine, bromine, iodine, fluorine, trifluoromethyl, hydroxy, cyano, aminomethyl or nitro;

(6) acyl groups of the formula:

Ar—G—CQQ'—CO— in which G is oxygen or sulfur; and Ar, Q and Q' are as defined above;

(7) acyl groups of the formula:

Ar—CHT—CO— in which Ar is defined above; and T is (i) amino, ammonio, amino protected by conventional amino protecting groups [for example, benzyloxycarbonyl, $C_2$ to $C_4$ alkoxycarbonyl, cyclopentyloxycarbonyl, cyclohexyloxycarbonyl, benzhydryloxycarbonyl, cyclopropylmethoxycarbonyl, methanesulfonylethoxycarbonyl, triphenylmethyl, 2,2,2-trichloroethoxycarbonyl, guanidylcarbamoyl, optionally substituted ureido carbonyl, $C_1$ to $C_5$ alkanoyl, pyroncarbonyl, thiopyridonecarbonyl, pyridonecarbonyl, homo- or heterocyclic monocyclic aromatic acyl (optionally substituted by hydroxy, $C_1$ to $C_3$ alkanoyloxy, halogen, trifluoromethyl, $C_1$ to $C_3$ alkyl, $C_1$ to $C_3$ aminoalkyl or $C_1$ to $C_3$ hydroxyalkyl)] or amino protected in the forms of phthalimido or enamino derived from acetoacetates, acetylacetone, or acetoacetamide; (ii) hydroxy or $C_1$ to $C_7$ acyloxy; (iii) carboxy or $C_2$ to $C_7$ alkoxycarbonyl, indanyloxycarbonyl, phenoxycarbonyl; or (iv) azido, cyano, carbamoyl, alkoxysulfonyl, sulfo, aminosulfonyl or alkoxysulfonyl; or HT combined represent hydroxyimino or alkoxyimino;

(8) $C_3$ to $C_5$ 2-sydnon-3-alkanoyl;

(9) (2- or 4-pyridon-1-yl)acetyl;

(10) 5-aminoadipoyl, 5-aminoadipoyl protected at the amino by $C_1$ to $C_{10}$ alkanoyl, $C_1$ to $C_5$ chloroalkanoyl or $C_2$ to $C_{10}$ alkoxycarbonyl; or 5-aminoadipoyl protected at the carboxy by benzhydryl, 2,2,2-trichloroethyl, trialkylsilyl, $C_1$ to $C_6$ alkyl, nitrobenzyl or methoxybenzyl; and

(11) acyl groups of the formula:

$$L-O-CO-$$

in which L is an easily removable optionally substituted $C_1$ to $C_8$ hydrocarbon group (e.g. 2,2,2-trichloroethyl, isobornyl, tertiary butyl, 1-methylcyclohexyl, 2-alkoxy-tertiary butyl, benzyl, p-nitrobenzyl or p-methoxybenzyl).

Alternatively, A and B considered together can represent a diacyl group derived from a polybasic $C_4$ to $C_{12}$ carboxylic acid, $C_1$ to $C_6$ alkylidene or $C_7$ to $C_9$ arylmethylidene.

In the above, examples of Ar groups are furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl and dihydrophenyl, each being optionally substituted by halogen, $C_1$ to $C_3$ alkyl, hydroxy, $C_1$ to $C_3$ alkoxy or aminomethyl.

The carboxy-protecting group which may be shown by X can contain up to 20 carbon atoms and can be an oxygen function such as, for example, $C_1$ to $C_8$ alkoxy (e.g. methoxy, ethoxy or t-butoxy), $C_7$ to $C_{20}$ aralkoxy (e.g. benzyloxy, methoxybenzyloxy, nitrobenzyloxy, diphenylmethoxy or trityloxy), mono- or di-cyclic aryloxy (e.g. phenoxy or naphthyloxy), or organometaloxy (e.g. trimethylstannyloxy or trimethylsilyloxy), $C_1$ to $C_8$ organic or inorganic acyloxy or metal oxy of groups I, II or III in the periodical table (e.g. sodiooxy, potassiooxy or magnesiodioxy); or X may be selected from sulfur functions such as those forming thiol ester, thiocarboxy or like groups; nitrogen functions such as those forming amides, hydrazides, azide or like groups; or X may be selected from other carboxy-protecting groups. These groups can, where possible, be interrupted by a hetero atom in their skeleton, or can be unsaturated or they can be substituted by a substituent such as those referred to above (e.g. the nitrogen, oxygen, sulfur, carbon or phosphorus functions referred to above or halogen). Among carboxy-protecting groups X are those forming $C_1$ to $C_5$ haloalkyl esters, $C_2$ to $C_{10}$ acylalkyl esters, $C_2$ to $C_8$ alkoxyalkyl or aminoalkyl esters, $C_2$ to $C_8$ acyloxyalkyl esters, $C_3$ to $C_8$ carbalkoxyalkyl esters, the phenyl ester, $C_7$ to $C_{20}$ aralkyl esters, esters with $C_2$ to $C_{10}$ oxim, $C_1$ to $C_5$ N-alkoxyamide, imide with saccharin, imide with phthalimide, N,N'-diisobutylhydrazide, metal salts, $C_1$ to $C_6$ alkylamine salts, dicyclohexylamine salts or analogues thereof containing from 2 to 15 carbon atoms, or groups equivalent in effect to these groups (in the above, specified numbers of carbon atoms are for groups X).

Antibacterially preferred carboxy-protecting groups X include those which form acyloxymethyl esters, phenacyl esters, the benzaldoxim ester, the N,N-dimethylaminoethyl ester, alkali metal salts, alkaline earth metal salts, acylated alkaline earth metal salts, and other groups equivalent in effect to these groups. Preferred carboxy-protecting groups X include benzhydryloxy, p-nitrobenzyloxy, p-methoxybenzyloxy, 2,2,2-trichloroethoxy and alkali metal-oxy.

Y can be a hydrogen or methoxy.

The compounds of formula (I) have been found to be very effective as antibacterial compounds against many bacteria and are superior to the corresponding 1-thia or natural cephalosporins. The compounds can be used as bactericides for combatting bacterial infections in humans or other animals, or the decay of perishables. For human use, the compounds can be administered at a dose of 0.1 to 5 g/day/man. Administration may be orally or parenterally and may be in the form of any conventional pharmaceutical formulation types, and may be in admixture with suitable carriers if required.

The present invention includes a pharmaceutical or veterinary formulation which comprises a compound of formula (I) formulated for pharmaceutical or veterinary use and preferably in unit dosage form (e.g. tablets, capsules, pills, a suspension or solution or a powder).

The invention further provides a pharmaceutical or veterinary composition which comprises a compound of formula (I) and a pharmaceutically or veterinarily acceptable, respectively, diluent, carrier or excipient. Such compositions may be in unit dosage form.

The new process for the preparation of the compound (I) is illustrated in SCHEME I below. However, it is to be understood that the positions of individual reactions can be altered where preferred and possible. It will be appreciated that the compounds of formulae (15) and (16) are also compounds of formula (I).

Among the reactions, the introduction of a propargyloxy group at position 2 of the azetidine ring to form compound (8) gives predominantly the 2,3-cis isomer (in the ratio of up to about 2:1 or more) in contrast to the cases where the 3-amino group is acylated where the reaction gives exclusively or predominantly the isomer having the 2,3-trans configuration leading to an ineffective final product (16) having a 6β-hydrogen. In the present process, introduction of the propargyloxy group precedes acylation of the amino group (when the acylation step is included). Furthermore, among procedures for the introduction of a propargyloxy at position 2 of the azetidine ring to form a compound (8), that using zinc chloride is superior to that using silver tetrafluoroborate from the view point of higher yields, or improved ratio of the desired isomer and inexpensive production.

The present invention includes a process for the preparation of a compound of the formula:

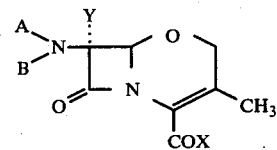

(wherein A and B are each hydrogen or an amino-protecting group;

X is hydroxy or a carboxy-protecting group; and

Y is hydrogen or methoxy) which process comprises converting a compound of the formula:

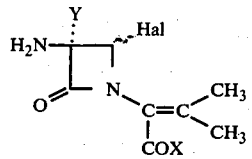

(wherein Hal is halogen and X and Y are as defined above) to produce the desired compound by means of a series of steps substantially as set out in SCHEME I; provided that the acylation step is optional and is not employed when both A and B are hydrogens in the final end product and the deprotection step is also optional and is not employed when X is a carboxy-protecting group in the final end product; and also provided that the order of the individual steps may be altered from SCHEME I where possible.

The invention includes within its scope the products of the above defined processes in so far as they have been made by that process.

The present process from compounds (8) to (10) is somewhat analogous to the method of Naylor et al (Journal of Chemical Society, 1973, 57) of the Beecham Group; the present process from compounds (10) to (15) is also somewhat analogous to the method disclosed in our copending British Patent Application No. 39614/75; provided that the above listed references relate to 1-thia instead of 1-oxacephalosporins. The step of the present process from compounds (15) to (16) is a procedure which is conventional in the art.

SCHEME I

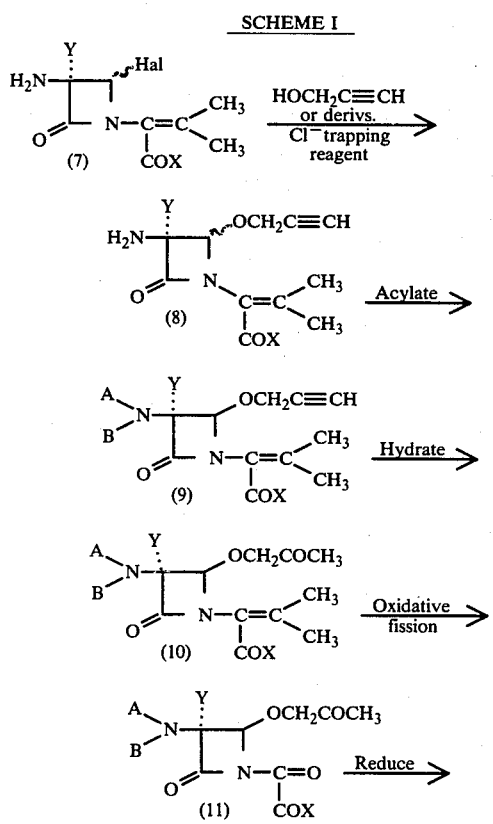

-continued
SCHEME I

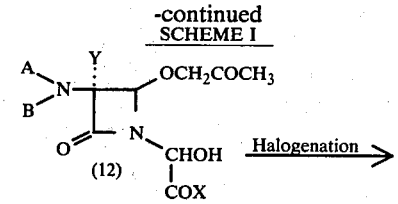

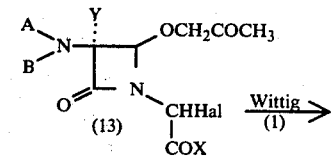

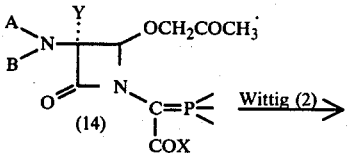

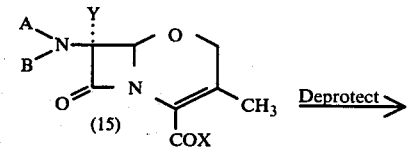

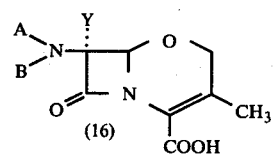

One embodiment of the present invention is the cephalosporin analogues represented by formula (I) wherein A is phenylacetyl, D-mandeloyl, α-phenylmalonyl, D-α-(3-methanesulfonyl-2-oxo-imidazolidin-1-yl)carbonamido-α-phenylacetyl, or 2-thienylacetamido; B is hydrogen; X is hydroxy; and Y is hydrogen, and pharmaceutically acceptable salts and esters thereof (such as the types of salts and esters outline above).

Among the said cephalosporin analogues, the compound represented by the following formula is a remarkable antibacterial:

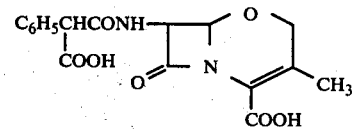

in the forms of free acid, pharmaceutically acceptable salts and esters (especially diphenylmethyl esters).

The above specific compound, 7β-(α-carboxy-phenylacetamido)-3-methyl-1-oxadethia-3-cephem-4-carboxylic acid, shows when assayed in vitro, strong antibacterial activity against gram negative bacteria even at higher inoculum size than $10^8$, and especially against strains of Escherichia coli resistant to many penicillins and cephalosporins. Its remarkable character is also demonstrated by its strong activity against Enterobacteria to which almost all penicillins and cephalosporins are inactive at a concentration of 100μ/ml.

The above specific compound can be prepared by acylating 7-amino-3-methyl-1-oxadethia-3-cephem-4-carboxylic acid or its esters with a reactive derivative of α-phenylmalonic acid, followed, if required, by deprotection and purification according to conventional methods.

The compound (I) wherein the acyl group represented by A or B is phenylacetyl is superior to the corresponding 1-thia compound, i.e. 7-phenylacetamidodeacetoxycephalosporanic acid, especially in its exceeding potency against typical gram negative bacteria.

The present invention includes a method for preventing or inhibiting the growth of bacteria in an environment which comprises administering to the environment an effective amount of a compound of formula (I) or of a formulation or composition in accordance with the invention. The method may be used for the treatment or prevention of infection in an animal, for the prevention or decay in a perishable material or for the disinfection of a substance, an article or a building structure.

The following description is given to provide an Example of the preparation of the compounds (I) according to SCHEME I. In the Example

is phenylacetamido; X is diphenylmethoxy; Y is hydrogen; and

is triphenylphosphoranilidene. In the NMR data the Hz values in parentheses are coupling constants.

The interconversion of some compounds (I) is also described in the following Example, starting from compound (16).

Diphenylmethyl α-[2β and 2α-chloro-3β-amino-4-oxoazetidin-1-yl]-α-isopropylideneacetate (7)

To a solution of crude diphenylmethyl α-(2β-methylthio-3β-amino-4-oxoazetidin-1-yl)-α-isopropylideneacetate toluene-p-sulfonate salt (5) (13.48 g; 20 mmole) in methylene chloride (100 ml) is added a solution of chlorine in carbon tetrachloride (1.34 Mole/liter; 19.4 ml; 36 mmole) at −78° C. The mixture is stirred at −78° C. for 20 minutes and at 0° C. for 20 minutes, and evaporated under reduced pressure. The residue is triturated thrice in a mixture of ether and petroleum ether, and evaporated to give crude diphenylmethyl α-[2β and 2α-chloro-3β-amino-4-oxoazetidin-1-yl]-α-isopropylideneacetate toluene-p-sulfonate salt (6) as yellow foam (13.45 g).

The product is treated with aqueous solution of sodium hydrogen carbonate and extracted with dichloromethane to give crude diphenylmethyl α-[2β and 2α-chloro-3β-amino-4-oxoazetidin-1-yl]-α-isopropylideneacetate (7) as yellow brown heavy syrup (9.50 g) (From its NMR spectrum, the ratio of 2β and 2α-chloro isomers was estimated to be about 4:1). Separation of a part of the crude product (2.50 g) by chromatography over silica gel containing 10% water (100 g) gives from the fraction eluted with a mixture of benzene and ethyl acetate (3:1), a (1:1) mixture of 2α and 2β-chloro isomers (120 mg), and pure 2β-chloro isomer (480 mg).

2α-chloro isomer:
NMR: $\delta^{CDCl_3}$ 1.98s3H, 2.25s3H, 2.83br-s2H, 4.33d(1.2Hz)1H, 5.47d(1.2Hz)1H, 6.90s1H, 7.30s10H (Estimated from NMR of mixture).

2β-chloro isomer:
IR: $\nu_{max}^{CHCl_3}$ 3425, 3370, 1787, 1730 cm$^{-1}$.
NMR: $\delta^{CDCl_3}$ 1.98s3H, 2.25s3H, 2.80br-s2H, 4.50d(4.0Hz)1H, 5.87d(4.0Hz)1H, 6.90s1H, 7.30s10H.

Diphenylmethyl α-[2β and 2α-(2-propynyloxy)-3β-amino-4-oxoazetidin-1-yl]-α-isopropylideneacetate (8)

(1) To a solution of crude diphenylmethyl α-[2β and 2α-chloro-3β-amino-4-oxoazetidin-1-yl]-α-isopropylideneacetate (7) (0.95 g) in a mixture of propargyl alcohol (3 ml) and tetrahydrofuran (2 ml) is added silver tetrafluoroborate (0.79 g; 4 mmole), and the mixture is stirred at room temperature for 3 hours. The reaction mixture is diluted with benzene (50 ml), cooled to 0° C., and stirred with a mixture of 5% aqueous solution of sodium hydrogen carbonate (10 ml) and saturated saline (5 ml). The mixture is filtrated through a layer of Celite, and filtrate is separated. The benzene layer is dried over sodium sulfate, concentrated under reduced pressure to give brown heavy oil, and purified by chromatography over silica gel containing 10% water (50 g) gives 2α-propynyloxy derivative (134 mg) and 2β-propynyloxy derivative (134 mg) from fractions eluted with a mixture of benzene and ethyl acetate (1:1).

2α-propynyloxy isomer:
IR: $\nu_{max}^{CHCl_3}$ 3400, 3320, 2115, 1767, 1723 cm$^{-1}$.
NMR: $\delta^{CDCl_3}$ 1.83br-s2H, 1.98s3H, 2.22s3H, 2.33t(2.5Hz)1H, 4.07d (2.5Hz)2H, ca. 4.07d1H, 4.93d(1.0Hz)1H, 6.90s1H, 7.32s10H.

2β-propynyloxy isomer:
IR: $\nu_{max}^{CHCl_3}$ 3410, 3320, 2115, 1767, 1720 cm$^{-1}$.
NMR: $\delta^{CDCl_3}$ 1.77br-s2H, 2.00s3H, 2.23s3H, 2.27t(2.5Hz)1H, 4.12d (2.5Hz)2H, 4.23d(4.0Hz)1H, 5.27d(4Hz)1H, 6.90s1H, 7.32s10H.

(2) To a solution of crude diphenylmethyl α-[2β and 2α-chloro-3β-amino-4-oxoazetidin-1-yl]-α-isopropylideneacetate (7) (0.95 g) in propargyl alcohol (5 ml) is added fused zinc chloride (818 mg; 6 mmole), and the mixture is stirred for 2 hours at room temperature. The reaction mixture is diluted with benzene (50 ml), cooled to 0° C., shaken with 5% aqueous sodium hydrogen carbonate (30 ml), and stirred vigorously. The mixture is filtered through a layer of Celite to remove separated solid, and the filtrate is separated. The benzene layer is dried over sodium sulfate, and evaporated under reduced pressure to leave brown heavy oil. Purification of the residue by chromatography over silica gel containing 10% water (50 g) gives starting material (107 mg), 2α-propynyloxy isomer (106 mg), and 2β-propynyloxy isomer (213 mg) from the fraction eluted with a mixture of benzene and ethyl acetate (1:1).

(3) The reaction of above (1) and (2) can be carried out by using sodium iodide, stannous chloride, and silver perchlorate in place of zinc chloride or silver tetrafluoroborate.

Diphenylmethyl α-[2β-(2-propynyloxy)-3β-phenylacetamido-4-oxoazetidin-1-yl]-α-isopropylideneacetate (9)

To a solution of diphenylmethyl α-[2β-(2-propynyloxy)-3β-amino-4-oxoazetidin-1-yl]-α-isopropylideneacetate (8) (2.039 g; 5.04 mmole) in methylene chloride (15 ml) are added phenylacetyl chloride (1.00 ml; 7.56 mmole) and pyridine (0.61 ml; 7.56 mmole) at 0° C. with stirring. The mixture is stirred at 0° C. for 30 minutes, mixed with ice water, and extracted with methylene chloride. The methylene chloride layer is washed with water, dried over sodium sulfate, and evaporated under reduced pressure. Purification of the residue by chromatography over silica gel containing 10% water (100 g) using a mixture of benzene and ethyl acetate (3:1) as eluting solvent gives the product (9) as pale yellow foam (2.242 g; 85.1%).

IR: $\nu_{max}^{CHCl_3}$ 3425, 1680, 1510, 3310, 2115, 1773, 1720 cm$^{-1}$.

NMR: $\delta^{CDCl_3}$ 1.98s3H, 2.25s3H, 2.23t(2.5Hz)1H, 3.58s2H, 3.95d (2.5Hz)2H, 5.32–5.52m2H, 6.50d(10Hz)1H, 7.00s1H, 7.35–7.40m15H.

Diphenylmethyl α-(2β-acetonyloxy-3β-phenylacetamido-4-oxoazetidin-1-yl)-α-isopropylideneacetate (10)

To a solution of diphenylmethyl α-[2β-(2-propynyloxy)-3β-phenylacetamido-4-oxoazetidin-1-yl]-α-isopropylideneacetate (9) (2.236 g; 4.28 mmole) in methanol (20 ml) is added water (2 ml). To this solution is added a saturated solution of mercuric sulfate in 10% sulfuric acid (0.8 ml), and the mixture is refluxed for 30 minutes. The reaction mixture is cooled, diluted with ethyl acetate, and washed with water. The ethyl acetate layer is dried over sodium sulfate, and concentrated under reduced pressure. Purification of the residue by chromatography over silica gel containing 10% water (100 g) using a mixture of benzene and ethyl acetate (2:1) as eluting solvent give the product (10) as pale yellow foam (1.547 g; 66.9%).

IR: $\nu_{max}^{CHCl_3}$ 3425, 1676, 1510, 1774, 1735(shoulder), 1720 cm$^{-1}$.

NMR: $\delta^{CDCl_3}$ 1.83s3H, 1.97s3H, 2.23s3H, 3.60s2H, 3.60+3.97q (8Hz)2H, 5.03d(4Hz)1H, 5.27dd(4;8Hz)1H, 6.50d(8Hz)1H, 6.93s1H, 7.30+7.33m15H.

Diphenylmethyl α-(2β-acetonyloxy-3β-phenylacetamido-4-oxoazetidin-1-yl)glyoxalate (11)

To a solution of diphenylmethyl α-(2β-acetonyloxy-3β-phenylacetamido-4-oxoazetidin-1-yl)-α-isopropylideneacetate (10) (2.342 g; 4.33 mmole) in methylene chloride (40 ml) is introduced ozonized oxygen for 25 minutes at −78° C. Excess ozone is purged with nitrogen gas, and the mixture is mixed with dimethyl sulfide (3 ml), and stirred at −78° C. for 30 minutes, and at room temperature for 30 minutes. The reaction mixture is mixed with three drops of acetic acid, washed with water, dried over sodium sulfate, and evaporated under reduced pressure to give the product (11) as pale yellow foam (2.312 g).

IR: $\nu_{max}^{CHCl_3}$ 3420, 1680, 1507, 1822, 1733, 1707 cm$^{-1}$.

NMR: $\delta^{CDCl_3}$ 1.87s3H, 3.55s2H, 5.30–5.57m2H, 6.85d(8Hz)1H, 4.22s2H, 6.93s1H, 7.22+7.30m15H.

Diphenylmethyl α-(2β-acetonyloxy-3β-phenylacetamido-4-oxoazetidin-1-yl)glycolate (12)

To a solution of diphenylmethyl α-(2β-acetonyloxy-3β-phenylacetamido-4-oxoazetidin-1-yl)glyoxalate (11) (2.312 g) in a mixture of methylene chloride (10 ml) and glacial acetic acid (10 ml) is added activated zinc powder (2.50 g) with stirring, and the mixture is stirred for 3 hours at room temperature. The reaction mixture is filtered through a layer of Celite which is washed with methylene chloride. The filtrate is washed with water, dried over sodium sulfate, and evaporated under reduced pressure to give the product (12) as pale yellow foam (2.136 g) as a mixture of epimers at position α.

IR: $\nu_{max}^{CHCl_3}$ 3425, 1675, 1505, 3350, 1785, 1740 cm$^{-1}$.

Diphenylmethyl α-(2β-acetonyloxy-3β-phenylacetamido-4-oxoazetidin-1-yl)-α-chloroacetate (13)

To a solution of diphenylmethyl α-(2β-acetonyloxy-3β-phenylacetamido-4-oxoazetidin-1-yl)glycolate (12) (2.136 g) in anhydrous methylene chloride (20 ml) are added thionyl chloride (0.90 ml) and pyridine (0.33 ml) with stirring at 0° C. After stirring for 1 hour at 0° C., the mixture is poured into ice water, and extracted with ethyl acetate. The organic layer is washed with water, dried over sodium sulfate, and evaporated under reduced pressure to give the crude product (13) (2.251 g) as brown foam of a mixture of epimers at position α.

IR: $\nu_{max}^{CHCl_3}$ 3430, 1680, 1510, 1795, 1752, 1740(shoulder) cm$^{-1}$.

Diphenylmethyl α-(2β-acetonyloxy-3β-phenylacetamido-4-oxoazetidin-1-yl)-α-triphenylphosphoranylideneacetate (14)

To a solution of crude diphenylmethyl α-(2β-acetonyloxy-3β-phenylacetamido-4-oxoazetidin-1-yl)-α-chloroacetate (13) (2.251 g) in anhydrous methylenechloride (20 ml) is added triphenylphosphine (1.50 g), and the mixture is refluxed for 4 hours under nitrogen atmosphere. The reaction mixture is poured into ice water, mixed with 5% aqueous solution of sodium hydrogen carbonate (20 ml), and extracted with methylene chloride. The organic layer is washed with water, dried over sodium sulfate, and evaporated under reduced pressure. Purification of the residue by chromatography over silica gel containing 10% water (100 g) using a mixture of benzene and ethyl acetate (1:2) as eluting solvent gives the product (14) (2.328 g) as yellow foam.

IR: $\nu_{max}^{CHCl_3}$ 3433, 1675, 1507, 1770, 1735, 1628 cm$^{-1}$.

Diphenylmethyl 1-oxadethia-3-methyl-7-phenylacetamido-3-cephem-4-carboxylate (15)

A solution of diphenylmethyl α-(2β-acetonyloxy-3β-phenylacetamido-4-oxoazetidin-1-yl)-α-triphenylphosphoranylideneacetate (14) (2.328 g) in anhydrous dioxane (30 ml) is refluxed for 64 hours under nitrogen atmosphere, and evaporated under reduced pressure to remove dioxane. The residue is purified by chromatography over silica gel containing 10% water (150 g) using a mixture of benzene and ethyl acetate (1:1) as developing solvent to give the product (15) (1.103 g; 74.7%). Crystallization of the product from ether gives pure colorless crystals of compound (15). m.p. 106°–107° C.

IR: $\nu_{max}^{CHCl_3}$ 3428, 1679, 1510, 1792, 1721 cm$^{-1}$.

NMR: $\delta^{CDCl_3}$ 1.93s3H, 3.63s2H, 4.03s2H, 4.95d(4Hz)1H, 5.68dd (4;9Hz)1H, 6.67d(9Hz)1H, 6.92s1H, 7.33+7.38m15H.

$[\alpha]_D^{25}$ −62.7°±1.9° (c=0.533, CHCl$_3$).

UV: $\nu_{max}^{CH_2Cl_2}$ 267.5 nm ($\epsilon$=7760).

1-Oxadethia-3-methyl-7-phenylacetamido-3-cephem-4-carboxylic acid (16)

To a solution of diphenylmethyl 1-oxadethia-3-methyl-7-phenylacetamido-3-cephem-4-carboxylate (15) (66 mg) in methylene chloride (3 ml) are added anisole (0.2 ml) and trifluoroacetic acid (0.2 ml) with stirring at 0° C., and the mixture is stirred at 0° C. for 2 hours. The reaction mixture is concentrated under reduced pressure to dryness, and the residue is dissolved in aqueous 5% sodium hydrogen carbonate solution, and washed with ether. The aqueous layer is acidified with 2N-hydrochloric acid, and is extracted with ethyl acetate. The organic layer is washed with water, dried over sodium sulfate, and evaporated under reduced pressure. Crystallization of the residue from a mixture of methylene chloride and petroleum ether gives the product (16) (30 mg) as colorless crystals. m.p. 180°–182° C. (with decomposition).

IR: $\nu_{max}^{KBr}$ 3404, 1778, 1650, 1536 cm$^{-1}$.

Diphenylmethyl 1-oxadethia-7-amino-3-methyl-3-cephem-4-carboxylate (17)

To a solution of diphenylmethyl 1-oxadethia-7-phenylacetamido-3-methyl-3-cephem-4-carboxylate (15) (600 mg; 1.243 mmole) in methylene chloride (15 ml) are added phosphorus pentachloride (518 mg; 2.486 mmole) and pyridine (0.181 ml; 2.486 mmole) at −20° C., and the mixture is stirred for 30 minutes at −20° C. and at room temperature for 45 minutes. To this solution is added methanol (10 ml), stirred for 30 minutes, diluted with water, and stirred for 30 minutes at room temperature. The reaction mixture is concentrated under reduced pressure, neutralized with 5% sodium hydrogen carbonate solution in the presence of ice, and extracted with ethyl acetate. The ethyl acetate layer is washed with water, dried over sodium sulfate, and evaporated under reduced pressure to give pale yellow foam. Purification of the foam by chromatography over silica gel containing 10% water (50 g) using a mixture of ethyl acetate and benzene (2:1) as eluting solvent gives the product (17) as colorless foam (367 mg).

IR: $\nu_{max}^{CHCl_3}$ 3420, 3350, 1787, 1720 cm$^{-1}$.

NMR: $\delta^{CDCl_3}$ 1.75s2H, 2.02s3H, 4.33s2H, 4.48d(4Hz)1H, 5.00d(4Hz)1H, 6.97s1H, 7.40m10H.

Diphenylmethyl 1-oxadethia-7-N-tertiary butoxycarbonyl-D-α-phenylglycinamido-3-methyl-3-cephem-4-carboxylate (18)

To a solution of diphenylmethyl 1-oxadethia-7-amino-3-methyl-3-cephem-4-carboxylate (17) (150 mg; 0.412 mmole) in a mixture of tetrahydrofuran (8 ml) and acetone (4 ml) are added N-tertiary butoxycarbonyl-D-α-phenylglycine (155 mg; 1.5 × 0.412 mmole) and N-ethoxycarbonyl-2-ethoxy-1,2-dihydroquinoline (152 mg; 1.5 × 0.412 mmole), and the mixture is stirred at room temperature for 14 hours. The reaction mixture is diluted with ethyl acetate, washed with water, hydrochloric acid, sodium hydrogen carbonate aqueous solution, and water, dried over sodium sulfate, and evaporated to give pale yellow foam. Purification of the foam by chromatography over silica gel containing 10% water (30 g) using a mixture of benzene and ethyl acetate (2:1) gives the product (18) (248 mg).

IR: $\nu_{max}^{CHCl_3}$ 3430, 1695, 1510, 1800, 1720 cm$^{-1}$.

NMR: $\delta^{CDCl_3}$ 1.43s9H, 1.98s3H, 4.18s2H, 5.00d(4Hz)1H, 5.27d(7Hz)1H, 5.65q(4;8Hz)1H, 5.67d(7Hz)1H, 6.77d(8Hz)1H, +7.4 aromatic H.

1-Oxadethia-7-D-α-phenylglycinamido-3-methyl-3-cephem-4-carboxylic acid trifluoroacetate (19)

To a solution of diphenylmethyl 1-oxadethia-7-N-tertiary butoxycarbonyl-D-α-phenylglycinamido-3-methyl-3-cephem-4-carboxylate (18) (246 mg) in methylene chloride (1.5 ml) are added anisole (0.7 ml) and trifluoroacetic acid (1.5 ml), and the mixture is stirred at 0° C. for 80 minutes and at room temperature for 40 minutes, and concentrated under reduced pressure. The residue is treated with a mixture of ether and petroleum ether to give powder of the product (19) as pale yellow powder (180 mg). m.p. decomposition takes place from 135° C.

IR: $\nu_{max}^{KBr}$ 3410, 1775, 1675, 1527 cm$^{-1}$.

NMR: $\delta^{D_2O+DCl}$ 1.97s3H, 4.33s2H, 5.10d(3.8Hz)1H, 5.32s1H, 7.53s5H.

UV: $\lambda_{max}^{H_2O}$ 255 nm ($\epsilon$=7080).

Diphenylmethyl 1-oxadethia-7-D-mandelamido-3-methyl-3-cephem-4-carboxylate (20)

To a solution of diphenylmethyl 1-oxadethia-7-amino-3-methyl-3-cephem-4-carboxylate (17) (71.6 mg; 0.196 mmole) in ethyl acetate (8 ml) is added successively a solution of sodium hydrogensulfite in water (100 mg in 4 ml) and mandelic acid O-carboxyanhydride (52.5 mg; 1.5 × 0.196 mmole) with vigorous stirring at 0° C. After stirring for 1 hour at room temperature, the mixture is diluted with ethyl acetate, washed with water, dried over sodium sulfate, and concentrated under reduced pressure. The obtained pale yellow powder is purified by chromatography over silica gel containing 10% water (20 g) using a mixture of benzene and ethyl acetate (1:1) to give the product (20) (80.4 mg).

IR: $\nu_{max}^{CHCl_3}$ 3425, 1695, 1510, 1797, 1727 cm$^{-1}$.

NMR: $\delta^{CDCl_3}$ 1.97s3H, 3.92brs1H, 4.20s2H, 5.00d(4Hz)1H, 5.13s1H, 5.63q(4;9Hz)1H, 6.98s1H, to 7.4 aromatic H.

1-Oxadethia-7-D-mandelamido-3-methyl-3-cephem-4-carboxylic acid (21)

To a solution of diphenylmethyl 1-oxadethia-7-D-mandelamido-3-methyl-3-cephem-4-carboxylate (20) (78.4 mg) in methylene chloride (2 ml) are added anisole (0.3 ml) and trifluoroacetic acid (0.3 ml) at 0° C. and the mixture is stirred at 0° C. for 30 minutes, and is evaporated under reduced pressure. The residue is dissolved in aqueous solution of sodium hydrogen carbonate, and washed with ether. The aqueous layer is acidified with hydrochloric acid, and extracted with ethyl acetate. The extract solution is washed with water, dried over sodium sulfate, and evaporated under reduced pressure to dryness. The residue is triturated in a mixture of ether and petroleum ether to give pale yellow powder of the product (21) (25 mg). m.p. about 120° C. to about 135° C.

IR: $\nu_{max}^{KBr}$ 3400, 1781, 1712, 1673, 1524 cm$^{-1}$.

Compounds (17) and (19)

In a similar manner as are described above (8) to (16), the title compounds are prepared with suitable protection in forms of e.g. N-tertiary butoxycarbonyl and O-formyl groups at the reactive group in the acyl groups.

7-[D-2-(3-Methylsulfonyl-2-oxoimidazolidin-1-yl)carbonamido-2-phenylacetamido]-3-methyl-1-oxadethia-3-cephem-4-carboxylic acid (22)

To a solution of 7-(D-2-phenylglycinamido)-3-methyl-1-oxadethia-3-cephem-4-carboxylic acid trifluoroacetate (19; 63.5 mg) in a mixture of tetrahydrofuran (0.8 ml) and water (0.2 ml) is added triethylamine (40 μl). To the stirred mixture at 0° C. are added 3-methylsulfonyl-2-oxoimidazolidine (83 mg) and triethylamine (40 μl). After stirring at room temperature for 15 minutes, the mixture is acidified with 2N-hydrochloric acid, and mixed with water and ethyl acetate. The ethyl acetate layer is washed with water, and extracted with aqueous sodium hydrogen carbonate. The aqueous layer is acidified with 2N-hydrochloric acid, and extracted with ethyl acetate. The ethyl acetate layer is washed with water, dried over sodium sulfate, and evaporated to remove ethyl acetate. Trituration of the residue in ether gives the title compound (22:23 mg) as pale yellow powder. m.p. about 150°–170° C.

IR: $\nu_{max}^{Nujol}$ 3325, 1787, 1730, 1678, 1527, 1168 cm$^{-1}$.

Diphenylmethyl 7-(2-thienylacetamido)-3-methyl-1-oxadethia-3-cephem-4-carboxylate (23)

To a solution of diphenylmethyl 7-amino-3-methyl-1-oxadethia-3-cephem-4-carboxylate (17:85.5 mg; 0.235 mmole) in methylene chloride (3 ml) at 0° C. are added 2-thienylacetyl chloride (56.5 mg; 0.353 mmole) and pyridine (19 μl; 0.353 mmole), and the mixture is diluted with ethyl acetate, washed with water, dried over sodium sulfate, and concentrated under reduced pressure to remove ethyl acetate. Purification of the residue by chromatography over silica gel containing 10% water (20 g) using a mixture of benzene and ethyl acetate (2:1) as eluting solvent gives the title compound (23:111.9 mg) as pale yellow foam.

IR: $\nu_{max}^{CHCl_3}$ 3420, 1792, 1722, 1680, 1505 cm$^{-1}$.
NMR: $\delta^{CDCl_3}$ 1.95s3H, 3.83s2H, 4.13s2H, 4.97d(4Hz)1H, 5.67dd (4;9Hz)1H, 6.62d(9Hz)1H, 6.98s1H, 6.9–7.3m13H.

7-(2-Thienylacetamido)-3-methyl-1-oxadethia-3-cephem-4-carboxylic acid (24)

To a solution of diphenylmethyl 7-(2-thienylacetamido)-3-methyl-1-oxadethia-3-cephem-4-carboxylate (23; 110 mg) in methylene chloride (3 ml) at 0° C. are added anisole (0.3 ml) and trifluoroacetic acid (0.3 ml), and the mixture is stirred at 0° C. for 30 minutes. The reaction mixture is evaporated under reduced pressure to dryness, and triturated in a mixture of methylene chloride, ether, and petroleum ether to give the title compound (24; 51.5 mg) as pale yellow powder.
m.p. 180°–185° C. (with decomposition).

IR: $\nu_{max}^{Nujol}$ 3320, 1775, 1720, 1655, 1550 cm$^{-1}$.

Diphenylmethyl 7β-(α-diphenylmethoxycarbonyl-α-phenylacetamido)-3-methyl-1-oxadethia-3-cephem-4-carboxylate (25)

To a solution of diphenylmethyl 7-amino-3-methyl-1-oxadethia-3-cephem-4-carboxylate (85.6 mg; 0.235 mmole) in a mixture of tetrahydrofuran (6 ml) and acetone (3 ml) are added α-phenylmalonic acid monobenzhydryl ester (245 mg; 0.705 mmole) and N-ethoxycarbonyl-2-ethoxy-1,2-dihydroquinoline (174 mg; 0.705 mmole), and the mixture is stirred at room temperature for 4 hours. The reaction mixture is diluted with ethyl acetate, washed with water, diluted with hydrochloric acid, aqueous sodium hydrogen carbonate, and water, dried over sodium sulfate, and concentrated to give heavy syrup (241 mg). Purification of the syrup by chromatography over silica gel containing 10% water (30 g) using a mixture of ethyl acetate and benzene (1:4) for elution, and trituration in a mixture of ether and petroleum ether gives the title compound (25) as colorless foam (102.6 mg; 63%).

IR: $\nu_{max}^{CHCl_3}$ 3420, 3350, 1797, 1725, 1680, 1516 cm$^{-1}$.
NMR: $\delta^{CDCl_3}$ 1.93s3H, 4.10s2H, 4.68s2H, 4.90d(4Hz)1H, 5.60q(4; 10Hz)1H, 6.85s2H, ca. 7.25m.

7β-(α-Phenylmalonamido)-3-methyl-1-oxadethia-3-cephem-4-carboxylic acid (26)

To a solution of diphenylmethyl 7β-(α-diphenylmethoxycarbonyl-α-phenylacetamido)-3-methyl-1-oxadethia-3-cephem-4-carboxylate (25) (100 mg) in methylene chloride (3 ml) are added anisole (0.2 ml) and trifluoroacetic acid (0.2 ml) at 0° C., and the mixture is stirred at 0° C. for 2 hours. The reaction mixture is concentrated under reduced pressure to leave residue, which is treated in a mixture of ether and petroleum ether to give the title compound (26) as almost colorless powder (46 mg; 89%).

m.p. 115°–120° C.
IR: $\nu_{max}^{Nujol}$ ca. 3400–2300, 1776, 1720, 1630, 1525 cm$^{-1}$.

Sodium 7β-(α-phenylmalonamido)-3-methyl-1-oxadethia-3-cephem-4-carboxylate

The product of preceding example is dissolved in an aqueous solution of sodium hydrogencarbonate (0.001 N) and diluted with water to give a solution for antibacterial assay in vitro on Mueller Hinton agar plates. The result shows strong antibacterial activity against even gram negative bacteria including Pseudomonas strains resistant to usually available penicillins and cephalosporins.

What we claim is:
1. A process for the production of a compound of the formula

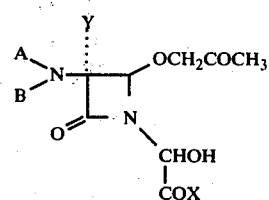

which comprises subjecting a compound of the formula

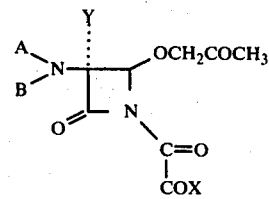

to reduction with at least one equivalent of zinc in acetic acid solvent in the presence or absence of an organic solvent, wherein, in said formulas, A and B each represents hydrogen or an amino-protecting group, X is hydroxy or a carboxy-protecting group and Y is hydrogen or methoxy.

2. A process for the production of a compound of the formula

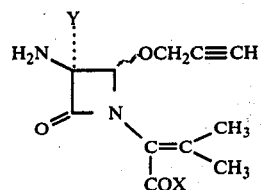

which comprises reacting a compound of the formula

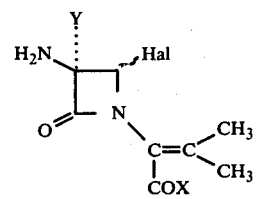

with a compound of the formula HOCH$_2$C≡CH in the presence of a halide trapping agent, wherein, in said formulas X represents hydroxy or a carboxy-protecting group, Y represents hydrogen or methoxy and Hal represents a halogen atom.

* * * * *